United States Patent
Kutzko et al.

(10) Patent No.: US 6,581,607 B2
(45) Date of Patent: *Jun. 24, 2003

(54) METHOD AND SYSTEM FOR USE IN TREATING A PATIENT WITH A BIOLOGICAL SUBSTANCE TO OPTIMIZE THERAPY AND PREVENT AN ADVERSE RESPONSE

(75) Inventors: John D. Kutzko, Nokomis, FL (US); John P. McMichael, Wexford, PA (US); Michaeal G. Singer, Harrisville, MI (US)

(73) Assignee: The Rx Files Corporation, Nokomis, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/916,411

(22) Filed: Jul. 27, 2001

(65) Prior Publication Data

US 2001/0042551 A1 Nov. 22, 2001

Related U.S. Application Data (63) Continuation-in-part of application No. 09/348,592, filed on Jul. 6, 1999, now Pat. No. 6,267,116, and a continuation-in-part of application No. 09/644,503, filed on Aug. 24, 2000, and a continuation-in-part of application No. 09/817,906, filed on Mar. 26, 2001, and a continuation-in-part of application No. 09/832,090, filed on Apr. 10, 2001.

(51) Int. Cl.$^7$ ............................................. A61B 19/00
(52) U.S. Cl. ...................................... 128/898; 600/300
(58) Field of Search .................. 128/897–98; 600/300, 600/308, 347, 364–66, 368

(56) References Cited

U.S. PATENT DOCUMENTS 6,267,116 B1 * 7/2001 McMichael ................. 128/898

* cited by examiner

Primary Examiner—John P. Lacyk
(74) Attorney, Agent, or Firm—Gifford, Krass, Groh, Sprinkle, Anderson & Citkowski, P.C.

(57) ABSTRACT

A method, system and apparatus for use in treating a patient receiving a biological substance, such as a cancer vaccine, to optimize therapy and prevent an adverse response. This system employs surrogate markers or indicators including blood levels of the vaccine to determine the next required dose for a patient. Since the surrogate markers may be employed as a percent change in status, virtually any indicator can be used. Surrogate markers could include any measure of the effectiveness of the vaccine's action. Given the effectiveness of the vaccine's action relative to the surrogate markers, a change in vaccine dose is calculated by the system. Conversely, by employing this system, one could determine the expected result of the vaccine dose change on the surrogate markers.

35 Claims, 2 Drawing Sheets

METHOD AND SYSTEM FOR USE IN TREATING A PATIENT WITH A BIOLOGICAL SUBSTANCE TO OPTIMIZE THERAPY AND PREVENT AN ADVERSE RESPONSE

RELATED APPLICATIONS

The present patent application is a continuation-in-part of the following U.S. patent applications: Ser. No. 09/348,592 filed on Jul. 6, 1999, which will issue as U.S. Pat. No. 6,267,116 on Jul. 31, 2001; Ser. No. 09/644,503 filed on Aug. 24, 2000 pending; Ser. No. 09/817,906 filed on Mar. 26, 2001 pending; and Ser. No. 09/832,090 filed on Apr. 10, 2001 pending; the entire contents of which applications are incorporated herein by reference thereto.

This document may contain material which is the subject of copyright protection. All rights in such copyrightable material are hereby reserved.

FIELD OF THE INVENTION

The present invention relates generally to a method and system for use in treating a patient with a biological substance to optimize therapy and to prevent an adverse response. More particularly, the present invention relates to a method and system for use in treating a patient with vaccines, serums, and/or drugs. The present invention can utilize either biological substance levels or other surrogate markers to determine the effectiveness of the dosing regimen and, if necessary, to suggest a new more optimal biological substance dose.

The term "biological substance" as used herein means all biological substances and includes, but is not limited to, vaccines, serums, drugs, adjuvants to enhance or modulate a resulting immune response, vitamin antagonists, medications, and all substances derived from and/or related to the foregoing substances.

Furthermore, wherever the generic term "biological substance" is used herein it is also intended to mean species which employ any or more of the individual biological substances as defined and/or alluded to herein.

The term "vaccine" or "vaccines" as used herein means all vaccines and includes, but is not limited to: autologous whole-cell vaccines (using cells derived from a patient's own tumor); allogenic whole-cell vaccines (using cancer cell lines established in vitro and then used to vaccinate multiple patients); tumor specific antigen/tumor associated antigen (TSA/TAA) based vaccines and hormonal autoimmunization approaches; all other cancer vaccines; Melacine; CancerVax; immune-boosting interferon; peptides; dendritic cells having melanoma protein thereon; interleukin-12; substances which stimulate or energize blood cells known as CD8 T cells; genes which make interleukin-12; tumor cells weakened by genes which make interleukin-12; substances which block blood-vessel formation to prevent growth of tumors; immunized cells; recombinant subunit vaccines; DNA vaccines; live recombinant viral vector vaccines; live recombinant bacterial vector vaccines; live-attenuated vaccines; whole-inactivated vaccines; virus-like particle vaccines; synthetic peptide vaccines; "Jennerian" vaccines; complex vaccines; and combinations of two or more of the foregoing.

The term "surrogate marker" as used herein means all surrogate markers and includes, but is not limited to: a measurement of biological activity within the body which indirectly indicates the effect of treatment on a disease state or on any condition being treated; and any measurement taken on a patient which relates to the patient's response to an intervention, such as the intervention of a biological substance introduced into or on the patient. For example, CD4 cell counts and viral load are examples of surrogate markers in HIV infection.

BACKGROUND OF THE INVENTION

When a patient begins taking a biological substance or any medication for a length of time, a titration of the amount of biological substance taken by the patient is necessary in order to achieve the optimal benefit of the biological substance, and at the same time to prevent any undesirable side effects that taking too much of the biological substance could produce. Thus, there is a continuous balance between taking enough of the biological substance in order to gain the benefits from that biological substance, and at the same time not taking so much biological substance as to illicit a toxic event.

There is large inter-individual variability in the patient biological interactions and/or the patient pharmocodynamic and pharmacokinetic interactions of biological substances. What may be an appropriate biological substance dose for one individual, may be too much or too little for another. A physician was required to estimate the correct biological substance dosage for a patient and then to experiment with that dosage, usually by trial and error, until the correct dosage was achieved. Likewise, the FDA labeling of a biological substance suggests dosages based on epidemiological studies and again does not account for inter-individual variability. Non-linear least squares modeling methods involve the use of large amounts of data relating to a general population in order to calculate a best fit. Much like linear regression models, this method cannot take into account the variability between people with the same population characteristics.

Bayesian analysis is another method used to relate biological substance dose to efficacy. This method employs large-scale population parameters to stratify a population in order to better characterize the individuals. This method does not take into account the changes that can occur within a person over time, and as a result cannot reliably estimate dosages.

Pharmacokinetic compartment modeling has had success with some biological substances, but because the models are static and cannot adapt themselves to changes within a population or a patient, they are once again undesirable for dynamically determining biological substance dosages.

Expert systems have been developed using similar technology to predict specific drug dosages for specific immunosuppressant drugs (see, e.g., U.S. Pat. Nos. 5,365,948, 5,542,436 and 5,694,950). These algorithms, however, are not generic and only use immunosuppressant blood levels. Each algorithm is specific to an individual specific immunosuppressant drug. As it stands, these inventions cannot be applied to other biological substances and do not have a non-linear feedback loop mechanism.

SUMMARY OF THE INVENTION

The present invention provides in one embodiment thereof a method for calculating a revised dose of a biological substance for a patient using said biological substance, comprising the steps of: accepting as a first input the patient's current biological substance dose; accepting as a second input a maximum dose of said biological substance; accepting as a third input a percent response of the patient based on one or more surrogate markers for said patient; and determining a revised dose, wherein said revised dose is a function of said current dose minus a ratio of the percent response of the patient and a ratio of said current dose to said maximum dose plus the percent of individual patient response multiplied by a response factor.

The present invention provides in another embodiment thereof a method for calculating a revised dose of a biological substance for a patient using said biological substance comprising the steps of: accepting as a first input the patient's current biological substance dose; accepting as a second input the maximum dose of the biological substance; accepting as a third input one or more numerical markers indicating a response of the patient; and calculating said revised dose, wherein said revised dose is a function of said current dose minus the ratio of the change in numerical markers and the ratio of said current dose to said maximum dose plus the percent of individual patient response multiplied by a response factor. According to the present invention, patient dosing occurs through a cyclic series of events, depicted in flow chart form in FIG. 1. After an initial examination, an initial dose of a biological substance, such as a cancer vaccine, is prescribed and administered by a physician for a patient. The initial dose is based on the FDA recommended dosage found on the biological substance label. The biological substance dose is further refined upon repeated dosing by the physician based on the patient's response to the biological substance. Too much biological substance could cause the patient to experience toxic biological substance effects, and the biological substance dose would need to be reduced. Too little biological substance could cause the patient not to receive the benefit the biological substance therapy could offer, and the dosage would need to be increased.

A preferred embodiment of the invention requires that a physician determine the percentage of response by the patient to the biological substance based on the surrogate markers for that biological substance. A relationship is then employed which uses the input parameters described above to determine the next dose for the patient.

Each specie of the invention has two preferred embodiments; one which uses actual numerical surrogate markers to calculate a dose, and another embodiment that uses percentages as the numerical input for the surrogate markers.

DETAILED DESCRIPTION OF THE INVENTION

A method of this invention for use in treating a patient receiving a biological substance to optimize therapy and to prevent an adverse biological substance response can be implemented in two different embodiments, two of which will each be described separately.

Figure 1:
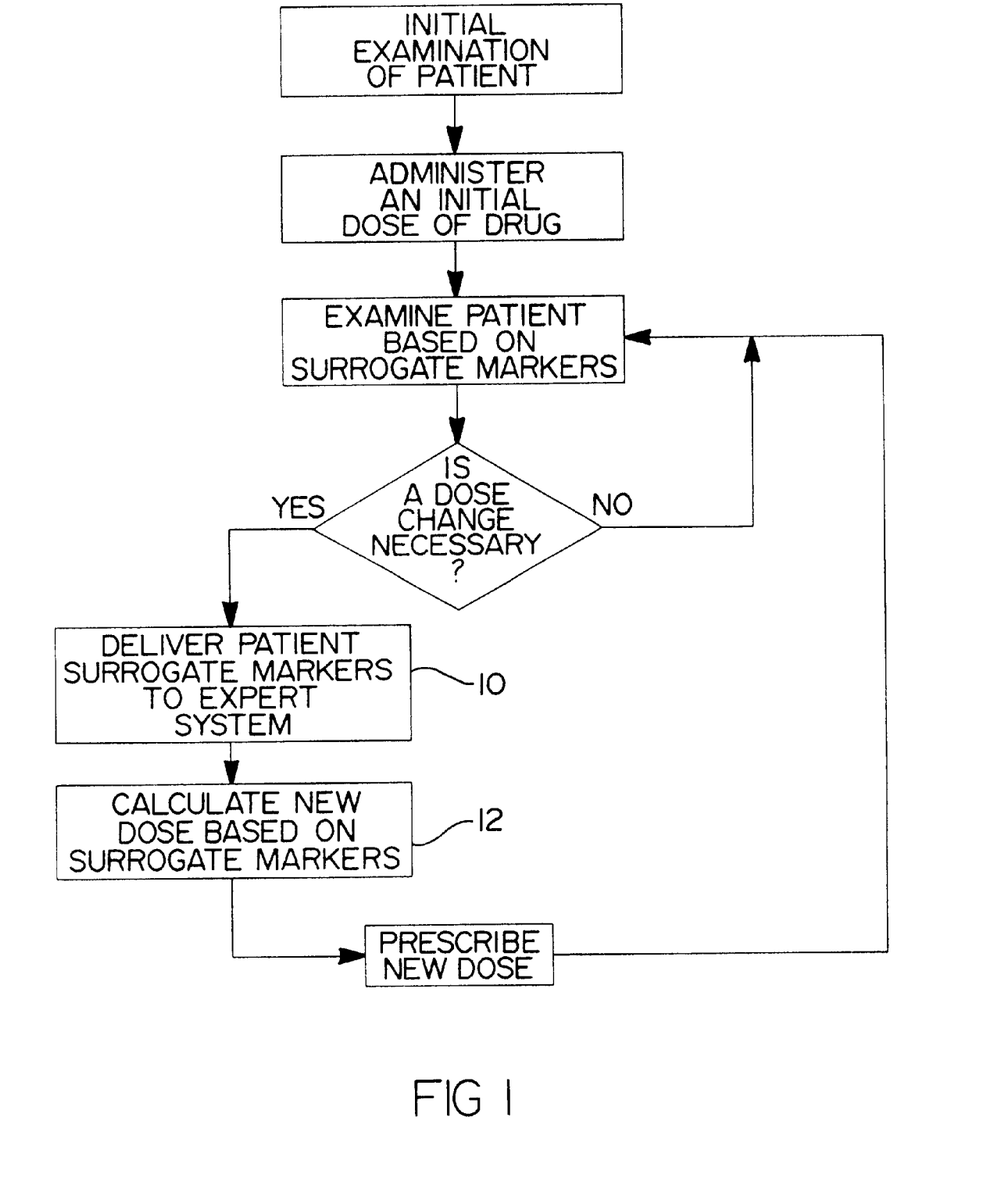
FIG. 1 shows a flow chart of the process by which revised doses of a biological substance are determined, according to the method of the invention described herein.

FIG. 1 shows a flow chart of the overall process of treating a patient using this expert system. The actual expert system, however, performs only the steps shown in blocks 10 and 12 of the flow chart.

Figure 2:
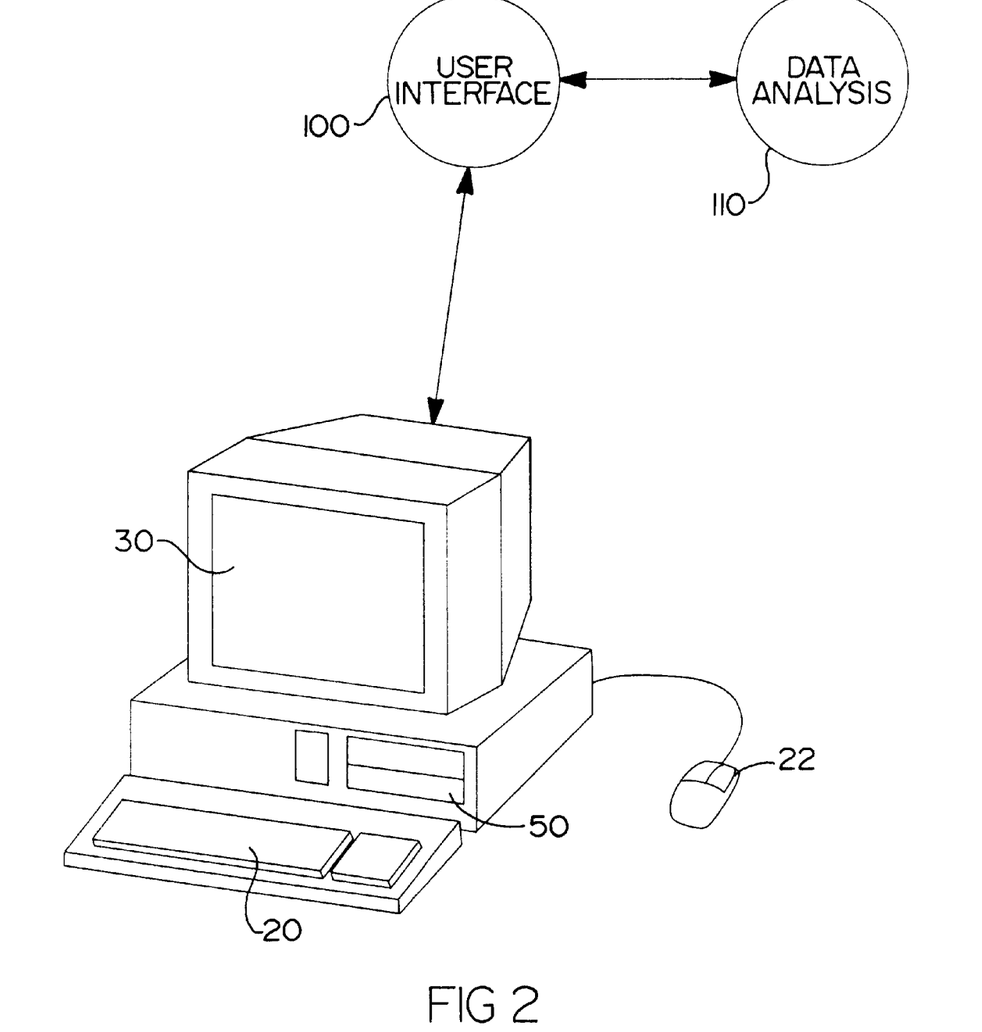
FIG. 2 shows an apparatus for use in calculating revised doses of a biological substance according to the present invention.

This expert system includes a general purpose computer, shown in FIG. 2, comprising an input means, preferably a keyboard 20 and/or a mouse 22, an output means 30, preferably a video display screen, a data storage means 50, preferably a hard disk drive, and a processor. The expert computer program receives input data from a physician regarding the patient's current biological substance dose, the maximal dose range for that particular biological substance, and the percent response of the patient based on the surrogate markers used to monitor that biological substance.

Also characterized is the patient's response to the last dosing cycle as well as a dose response constant. This allows the expert system to individualize the patient dosing based on the patient's individual response to that particular biological substance. The system calculates a revised dosage based on the data input by the physician.

The software portion of the invention includes a user interface portion 100 to receive the input data and to output the revised dosage information, and a data analysis portion 110, which calculates the new dosage information based on the input data.

Numerical Surrogate Markers Embodiment

A physician prescribes a biological substance for a patient based on the FDA recommended dose on the label of the biological substance. The physician then reevaluates the patient, usually daily, either in person or remotely depending on the biological substance being prescribed.

During the subsequent evaluations by the physician, the surrogate markers are monitored and sequentially compared to determine if there are any toxicities associated with the biological substance. Also the numerical markers will be evaluated to see if the desired effect of the biological substance is being achieved.

Based on this evaluation by the physician, the current biological substance dose, the current biological substance numerical marker, the desired biological substance numerical marker, and the previous biological substance numerical marker are then input into the embodiment and the new biological substance dose is calculated based on the equation:

$$NBD=CBD-\{[<(CBNM-DBNM)/CBNM>/<1+(CBD/HIGH)>]\times CBD\}+LV$$

where:

$LV=\{(RESPONSE \times CBD) \times [(1+D)-(1+E)]/abs(1+D)\}/1.3^{\wedge}(CBD/HIGH)$ $E=CBNM-PBNM$ $D=DBNM-PBNM$ and wherein:

NBD=New Biological Substance Dose

CBD=Current Biological Substance Dose

CBNM=Current Biological Substance Numerical Marker

DBNM=Desired Biological Substance Numerical Marker

PBNM=Previous Biological Substance Numerical Marker

HIGH=The input parameter that is the high dose range for said biological substance RESPONSE=Percent of total dose available for individualizing patient dose abs=The absolute value of $1.3^{\wedge}(CBD/HIGH)=1.3$ raised to an exponent of (CBD/HIGH).

Percentage Surrogate Markers Embodiment

In this preferred embodiment, a physician prescribes a biological substance for a patient based on the FDA recommended dose on the label of the biological substance. The physician then re-evaluates the patient, usually daily, either in person or remotely depending on the agent being prescribed.

During the subsequent evaluations by the physician, the surrogate markers are monitored and sequentially compared to determine if there are any toxicities associated with the biological substance. Also the surrogate markers are evaluated to see if the desired effect of the biological substance is being achieved.

Based on this evaluation by the physician, the current biological substance dose, and the percent response of the patient to the last dosing based on a surrogate marker are then input into the system and the new biological substance dose is calculated based on the equation:

$$NBD=CBD-\{[<(PBD-100)/PBD>/<1+(CBD/HIGH)>]\times CBD\}+LV$$

where:

$LV=\{(RESPONSE\times CBD)\times[(100-RES)\times 0.01]\}/1.3\char`\^(CBD/HIGH)$ and wherein:

NBD=New Biological Substance Dose

CBD=Current Biological Substance Dose

PBD=Percent response of patient to surrogate marker

RES=Percent response of patient to last dosing based on surrogate marker

HIGH=The input parameter that is the high dose range for said biological substance RESPONSE=Percent of total dose available for individualizing patient dose $1.3\char`\^(CBD/HIGH)=1.3$ raised to an exponent of (CBD/HIGH).

This cycle of repeated re-evaluation of the numerical surrogate markers is continued as long as the patient is required to take the biological substance.

Two embodiments of the invention have been described, one using numerical markers, and one using a percentage surrogate marker.

The invention thus provides methods, systems and apparatus for use in treating a patient receiving a biological substance or a substance, such as a cancer vaccine, to optimize therapy and prevent an adverse response. This system employs surrogate markers or indicators including blood levels of the biological substance to determine the next required dose for a patient. Since the surrogate markers may be employed as a percent change in status, virtually any indicator can be used. Surrogate markers could include any measure of the effectiveness of the biological substance's action.

Given the effectiveness of the biological substance's action relative to the surrogate markers, a change in biological substance dose is calculated by the system. Conversely, by employing this system, one could determine the expected result of the biological substance dose change on the surrogate marker.

EXAMPLE 1

Cancer Vaccine

A physician would give a cancer patient a standard amount of the cancer vaccine (based on meter squared calculation) by infusing the patient with cells impregnated with the vaccine and would then monitor the increased lymphocyte activity as a response to the introduction of the vaccine. This test is done by drawing a small amount of the patient's blood and performing a test on it that usually determines the rise in the cytotoxic T-lymphocyte (CTL) activity. The physician could also use the clinical state of the patient (i.e., progression of disease, increase in the vascularization or size of the tumor). Each of these two methods is used to determine the patient's response to the cancer vaccine therapy. This information (vaccine dose and response) along with the desired response are used in the next dose calculation by the methods in accordance with the present invention.

EXAMPLE 2

Alzheimer's Vaccine

It is believed that beta-amyloid causes the onset of Alzheimer's disease. A physician would give an Alzheimer's patient a standard amount of the beta-amyloid vaccine (based on meter squared calculation) by infusing the patient with cells impregnated with the vaccine and would then monitor the increased anti-beta-amyloid activity as a response to the introduction of the vaccine, i.e., an increase in the beta-amyloid binding antibodies. This test is done by drawing a small amount of the patient's blood and performing a test. This information (vaccine dose and response) along with the desired response are used in the next dose calculation by the methods in accordance with the present invention.

EXAMPLE 3

Biologics (Generally)

Dose:

Biologics, such as vaccines are delivered to the patient via cells (e.g., dendritic cells) the vaccine is impregnated into the cells. The cells are then delivered into the patient. Therefore the dose that a patient receives is dependant on the number of cells containing the biologic substance delivered to the patient, usually measured in millions of cells.

Response:

The response measured depends on the disease being treated. Here are some examples:

Nicotine vaccine: increase in the titres of nicotine specific antibodies.

Hepatitis B vaccine:

increase in the HBV antibodies or a decrease in the HBV antigen (shows presence of the disease).

Although the invention has been described in detail in the foregoing for the purpose of illustration, it is to be understood that such detail is solely for that purpose and that variations can be made therein by those of ordinary skill in the art without departing from the spirit and scope of the invention as defined by the following claims, including all equivalents thereof.

What is claimed is:

1. A method for calculating a revised dose of a biological substance for a patient using said biological substance, comprising the steps of:

accepting as a first input the patient's current biological substance dose;

accepting as a second input a maximum dose of said biological substance;

accepting as a third input a percent response of the patient based on one or more surrogate markers for said patient; and determining a revised dose, wherein said revised dose is a function of said current dose minus a ratio of the percent response of the patient and a ratio of said current dose to said maximum dose plus the percent of individual patient response multiplied by a response factor.

2. The method of claim 1, wherein:

said determining step includes determining said revised dose based on the equation $$RBD=CBD-\{[<(PBD-100)/PBD>/<1+(CBD/HIGH)>]\times CBD\}+LV$$

where:

$LV=\{(RESPONSE \times CBD) \times [(100-RES) \times 0.01]\}/1.3^{\wedge}(CBD/HIGH)$ and wherein:

RBD=Revised Biological Substance Dose
CBD=Current Biological Substance Dose
PBD=Percent response of patient to surrogate marker
RES=Percent response of patient to last dosing based on surrogate marker
HIGH=The input parameter that is the high dose range for said biological substance
RESPONSE=Percent of total dose available for individualizing patient dose
$1.3^{\wedge}(CBD/HIGH)=1.3$ raised to an exponent of (CBD/HIGH).

3. The method of claim 1, wherein:

said biological substance is selected from a group comprising vaccines, serums, drugs, all vitamin antagonists, and all substances derived from and/or related to the foregoing substances.

4. A method for calculating a revised dose of a biological substance for a patient using said biological substance comprising the steps of:

accepting as a first input the patient's current biological substance dose;

accepting as a second input the maximum dose of the biological substance;

accepting as a third input one or more numerical markers indicating a response of the patient; and calculating said revised dose, wherein said revised dose is a function of said current dose minus the ratio of the change in numerical markers and the ratio of said current dose to said maximum dose plus the percent of individual patient response multiplied by a response factor.

5. The method of claim 4, wherein:

said calculating step includes calculating said revised dose based on the equation $$RBD=CBD-\{[<(CBNM-DBNM)/CBNM>/<1+(CBD/HIGH)>]\times CBD\}+LV$$

where:

$LV=\{(RESPONSE \times CBD) \times [(1+D)-(1+E)]/abs\ (1+D)\}/1.3^{\wedge}(CBD/HIGH)$
$E=CBNM-PBNM$
$D=DBNM-PBNM$ and wherein:

RBD=Revised Biological Substance Dose
CBD=Current Biological Substance Dose
CBNM=Current Biological Substance Numerical Marker
DBNM=Desired Biological Substance Numerical Marker
PBNM=Previous Biological Substance Numerical Marker
HIGH=The input parameter that is the high dose range for said biological substance
RESPONSE=Percent of total dose available for individualizing patient dose
abs=The absolute value of
$1.3^{\wedge}(CBD/HIGH)=1.3$ raised to an exponent of (CBD/HIGH).

6. The method of claim 4, wherein:

said biological substance is selected from a group comprising vaccines, serums, drugs, all vitamin antagonists, and all substances derived from and/or related to the foregoing substances.

7. A method for determining a dose of a biological substance for a patient, comprising the steps of:

administering an initial dose of said biological substance to the patient;

evaluating the patient to monitor and characterize one or more numerical surrogate markers;

determining, based on said numerical surrogate markers, if a dose change for said biological substance is necessary; and calculating a revised dose as a function of said current dose minus the ratio of a percent response of the patient and the ratio of said current dose to said maximum dose plus the percent of individual patient response multiplied by a response factor.

8. The method of claim 7, wherein:

said biological substance is selected from a group comprising vaccines, serums, drugs, all vitamin antagonists, and all substances derived from and/or related to the foregoing substances.

9. A method for determining a dose of a biological substance for a patient, comprising the steps of:

administering an initial dose of said biological substance to the patient;

examining the patient to monitor and characterize one or more numerical surrogate markers;

determining if a dose change is necessary; and calculating a revised dose as a function of said current dose minus the ratio of the change in numerical markers and the ratio of said current dose to said maximum dose plus the percent of individual patient response multiplied by a response factor.

10. A method for calculating a revised dose of a biological substance for a patient currently using said biological substance, comprising the steps of:

accepting as input the patient's current biological substance dose;

accepting as input the maximum dose of said biological substance;

accepting as input the percent response of the patient based on surrogate markers; and calculating a revised dose, wherein said revised dose is a function of said current dose, said maximum dose, and said percent response of the patient based on said surrogate markers.

11. A method for calculating a revised dose of a biological substance for a patient currently using said biological substance, comprising the steps of:

accepting as input a patient's current biological substance dose;

accepting as input a maximum dose of said biological substance;

accepting as input the previous, current and desired values of one or more numerical surrogate markers indicating the response of the patient; and calculating a revised dose, wherein said revised dose is a function of said current dose, said maximum dose, and said previous, current and desired values of said numerical surrogate markers.

12. A storage device having stored thereon an ordered set of instructions which, when executed by a computer, performs a predetermined method, comprising:

first means for accepting as input a patient's current biological substance dose;

second means for accepting as input a maximum dose of said biological substance;

third means for accepting as input a percent response of a patient based on predetermined surrogate markers; and calculating a revised dose, wherein said revised dose is a function of said current dose minus the ratio of a percent response of the patient and the ratio of said current dose to said maximum dose plus the percent of individual patient response multiplied by a response factor.

13. The storage device of claim 12, wherein:

said biological substance is selected from a group comprising vaccines, serums, drugs, all vitamin antagonists, and all substances derived from and/or related to the foregoing substances.

14. A storage device having stored thereon an ordered set of instructions which, when executed by a computer, performs a predetermined method, comprising:

first means for accepting as input a patient's current biological substance dose;

second means for accepting as input the maximum dose of said biological substance;

third means for accepting as input one or more numerical surrogate markers indicating the response of said patient to said biological substance; and calculating a revised dose, wherein said revised dose is a function of said current dose minus the ratio of the change in said numerical surrogate markers and the ratio of said current dose to said maximum dose plus the percent of individual patient response multiplied by a response factor.

15. An apparatus for calculating a revised dose of a biological substance for a patient, comprising:

first means for accepting as input one or more surrogate markers which indicate a patient's response to a dose of said biological substance;

second means for accepting as input the patient's current biological substance dose;

third means for accepting as input the maximum dose of said biological substance; and fourth means for calculating a revised dose of said biological substance as a function of said surrogate markers, said current biological substance dose, and said maximum biological substance dose.

16. The apparatus of claim 15, wherein:
said surrogate markers are actual numerical markers.

17. The apparatus of claim 15, wherein:
said surrogate markers are surrogate markers representing a percent response of the patient to said biological substance.

18. The apparatus of claim 15, wherein:
said revised dose is calculated by the equation:

$$RBD=CBD-\{[<(CBNM-DBNM)/CBNM>/<1+(CBD/HIGH)>]\times CBD\}+LV$$

where:
$LV=\{(RESPONSE\times CBD)\times[(1+D)-(1+E)]/abs(1+D)\}/1.3^\wedge(CBD/HIGH)$
$E=CBNM-PBNM$
$D=DBNM-PBNM$ and wherein:
RBD=Revised Biological Substance Dose
CBD=Current Biological Substance Dose
CBNM=Current Biological Substance Numerical Marker
DBNM=Desired Biological Substance Numerical Marker
PBNM=Previous Biological Substance Numerical Marker
HIGH=The input parameter that is the high dose range for said biological substance
RESPONSE=Percent of total dose available for individualizing patient dose
abs=The absolute value of
$1.3^\wedge(CBD/HIGH)=1.3$ raised to an exponent of (CBD/HIGH).

19. The apparatus of claim 15, wherein:
said revised dose is calculated by the equation:

$$RBD=CBD-\{[<(PBD-100)/PBD>/<1+(CBD/HIGH)>]\times CBD\}+LV$$

where:
$LV=\{(RESPONSE\times CBD)\times[(100-RES)\times 0.01]\}/1.3^\wedge(CBD/HIGH)$ and wherein:
RBD=Revised Biological Substance Dose
CBD=Current Biological Substance Dose
PBD=Percent response of patient to surrogate marker
RES=Percent response of patient to last dosing based on surrogate marker
HIGH=The input parameter that is the high dose range for said biological substance
RESPONSE=Percent of total dose available for individualizing patient dose
$1.3^\wedge(CBD/HIGH)=1.3$ raised to an exponent of (CBD/HIGH).

20. The apparatus of claim 15, wherein:
said biological substance is selected from a group comprising vaccines, serums, drugs, all vitamin antagonists, and all substances derived from and/or related to the foregoing substances.

21. A method for calculating a revised dose of a vaccine for a patient using said vaccine, comprising the steps of:

accepting as a first input the patient's current vaccine dose;

accepting as a second input a maximum dose of said vaccine;

accepting as a third input a percent response of the patient based on one or more surrogate markers for said patient; and determining a revised dose, wherein said revised dose is a function of said current dose minus a ratio of the percent response of the patient and a ratio of said current dose to said maximum dose plus the percent of individual patient response multiplied by a response factor.

22. The method of claim 21, wherein:
said determining step includes determining said revised dose based on the equation $$RVD=CVD-\{[<(PVD-100)/PVD>/<1+(CVD/HIGH)>]\times CVD\}+LV,$$

where $LV=\{(RESPONSE \times CVD) \times [(100-RES) \times 0.01]\}/1.3^{\wedge}(CVD/HIGH)$ and wherein:

RVD=Revised Vaccine Dose

CVD=Current Vaccine Dose

PVD=Percent response of patient to surrogate marker

RES=Percent response of patient to last dosing based on surrogate marker

HIGH=The input parameter that is the high dose range for said vaccine

RESPONSE=Percent of total dose available for individualizing patient dose $1.3^{\wedge}(CVD/HIGH)=1.3$ raised to an exponent of (CVD/HIGH).

23. A method for calculating a revised dose of a vaccine for a patient using said vaccine comprising the steps of:

accepting as a first input the patient's current vaccine dose;

accepting as a second input the maximum dose of the vaccine;

accepting as a third input one or more numerical markers indicating a response of the patient; and calculating said revised dose, wherein said revised dose is a function of said current dose minus the ratio of the change in numerical markers and the ratio of said current dose to said maximum dose plus the percent of individual patient response multiplied by a response factor.

24. The method of claim 23, wherein:

said calculating step includes calculating said revised dose based on the equation $$RVD=CVD-\{[<(CVNM-DVNM)/CVNM>/<1+(CVD/HIGH)>] \times CVD\}+LV$$

where:

$LV=\{(RESPONSE \times CVD) \times [(1+D)-(1+E)]/abs(1+D)\}/1.3^{\wedge}(CVD/HIGH)$

E=CVNM−PVNM

D=DVNM−PVNM and wherein:

RVD=Revised Vaccine Dose

CVD=Current Vaccine Dose

CVNM=Current Vaccine Numerical Marker

DVNM=Desired Vaccine Numerical Marker

PVNM=Previous Vaccine Numerical Marker

HIGH=The input parameter that is the high dose range for said vaccine

RESPONSE=Percent of total dose available for individualizing patient dose abs=The absolute value of $1.3^{\wedge}(CVD/HIGH)=1.3$ raised to an exponent of (CVD/HIGH).

25. A method for determining a dose of a vaccine for a patient, comprising the steps of:

administering an initial dose of said vaccine to the patient;

evaluating the patient to monitor and characterize one or more numerical surrogate markers;

determining, based on said numerical surrogate markers, if a dose change for said vaccine is necessary; and calculating a revised dose as a function of said current dose minus the ratio of a percent response of the patient and the ratio of said current dose to said maximum dose plus the percent of individual patient response multiplied by a response factor.

26. A method for determining a dose of a vaccine for a patient, comprising the steps of:

administering an initial dose of said vaccine to the patient;

examining the patient to monitor and characterize one or more numerical surrogate markers;

determining if a dose change is necessary; and calculating a revised dose as a function of said current dose minus the ratio of the change in said numerical surrogate markers and the ratio of said current dose to said maximum dose plus the percent of individual patient response multiplied by a response factor.

27. A method for calculating a revised dose of a vaccine for a patient currently using said vaccine, comprising the steps of:

accepting as input the patient's current vaccine dose;

accepting as input the maximum dose of said vaccine;

accepting as input the percent response of the patient based on surrogate markers; and calculating a revised dose, wherein said revised dose is a function of said current dose, said maximum dose, and said percent response of the patient based on said surrogate markers.

28. A method for calculating a revised dose of a vaccine for a patient currently using said vaccine, comprising the steps of:

accepting as input a patient's current vaccine dose;

accepting as input a maximum dose of said vaccine;

accepting as input the previous, current and desired values of one or more numerical surrogate markers indicating the response of the patient; and calculating a revised dose, wherein said revised dose is a function of said current dose, said maximum dose, and said previous, current and desired values of said numerical surrogate markers.

29. A storage device having stored thereon an ordered set of instructions which, when executed by a computer, performs a predetermined method, comprising:

first means for accepting as input a patient's current vaccine dose;

second means for accepting as input a maximum dose of said vaccine;

third means for accepting as input a percent response of a patient based on predetermined surrogate markers; and calculating a revised dose, wherein said revised dose is a function of said current dose minus the ratio of a percent response of the patient and the ratio of said current dose to said maximum dose plus the percent of individual patient response multiplied by a response factor.

30. A storage device having stored thereon an ordered set of instructions which, when executed by a computer, performs a predetermined method, comprising:

first means for accepting as input a patient's current vaccine dose;

second means for accepting as input the maximum dose of said vaccine;

third means for accepting as input one or more numerical surrogate markers indicating the response of said patient to said vaccine; and calculating a revised dose, wherein said revised dose is a function of said current dose minus the ratio of the change in said numerical surrogate markers and the ratio of said current dose to said maximum dose plus the percent of individual patient response multiplied by a response factor.

31. An apparatus for calculating a revised dose of a vaccine for a patient, comprising:

first means for accepting as input one or more surrogate markers which indicate a patient's response to a dose of said vaccine;

second means for accepting as input the patient's current vaccine dose;

third means for accepting as input the maximum dose of said vaccine; and fourth means for calculating a revised dose of said vaccine as a function of said surrogate markers, said current vaccine dose, and said maximum vaccine dose.

32. The apparatus of claim 31, wherein:
said surrogate markers are actual numerical markers.

33. The apparatus of claim 31, wherein:
said surrogate markers are surrogate markers representing a percent response of the patient to said vaccine.

34. The apparatus of claim 31, wherein:
said revised dose is calculated by the equation:

$$RVD=CVD-\{[<(CVNM-DVNM)/CVNM>/<1+(CVD/HIGH)>]\times CVD\}+LV$$

where:
$LV=\{(RESPONSE \times CVD) \times [(1+D)-(1+E)]/abs(1+D)\}/1.3^{\wedge}(CVD/HIGH)$
$E=CVNM-PVNM$
$D=DVNM-PVNM$ and wherein:
RVD=Revised Vaccine Dose
CVD=Current Vaccine Dose
CVNM=Current Vaccine Numerical Marker
DVNM=Desired Vaccine Numerical Marker
PVNM=Previous Vaccine Numerical Marker
HIGH=The input parameter that is the high dose range for said vaccine RESPONSE=Percent of total dose available for individualizing patient dose abs=The absolute value of 1.3^(CVD/HIGH)=1.3 raised to an exponent of (CVD/HIGH).

35. The apparatus of claim 31, wherein:

said revised dose is calculated by the equation:

$$RVD=CVD-\{[<(PVD-100)/PVD>/<1+(CVD/HIGH)>]\times CVD\}+LV,$$

where:

LV={(RESPONSE×CVD)×[(100−RES)×0.01]}/1.3^(CVD/HIGH)

and wherein:

RVD=Revised Vaccine Dose

CVD=Current Vaccine Dose

PVD=Percent response of patient to surrogate marker

RES=Percent response of patient to last dosing based on surrogate marker

HIGH=The input parameter that is the high dose range for said vaccine

RESPONSE=Percent of total dose available for individualizing patient dose 1.3^(CVD/HIGH)=1.3 raised to an exponent of (CVD/HIGH).

* * * * *

UNITED STATES PATENT AND TRADEMARK OFFICE
CERTIFICATE OF CORRECTION

PATENT NO.    : 6,581,607 B2
DATED         : June 24, 2003
INVENTOR(S)   : John D. Kutzko It is certified that error appears in the above-identified patent and that said Letters Patent is hereby corrected as shown below:

<u>Title page,</u>
Item [56], References Cited, U.S. PATENT DOCUMENTS, insert:
-- 5,365,948      11/1994       McMichael     128/898
5,542,436         8/1996        McMichael     128/897
4,694,950         12/1997       McMichael     128/989 --

Signed and Sealed this

Twenty-seventh Day of January, 2004

JON W. DUDAS
*Acting Director of the United States Patent and Trademark Office*